US00PP08591P

United States Patent [19]

Warriner, deceased

[11] Patent Number: Plant 8,591

[45] Date of Patent: Feb. 15, 1994

[54] HYBRID TEA ROSE PLANT NAMED 'JACPAL'

[75] Inventor: William A. Warriner, deceased, late of Tustin, Calif., by Alene B. Warriner, legal representative

[73] Assignee: Bear Creek Gardens, Inc, Medford, Oreg.

[21] Appl. No.: 953,722

[22] Filed: Sep. 28, 1992

[51] Int. Cl.[5] ..... A01H 5/00

[52] U.S. Cl. ..... Plt./11

[58] Field of Search ..... Plt. 11, 12, 16

*Primary Examiner*—Howard J. Locker

*Attorney, Agent, or Firm*—Klarquist, Sparkman, Campbell, Leigh and Whinston

[57] ABSTRACT

A hybrid tea rose plant producing long-lasting, long-stemmed cut roses and having a vigorous, upright growth; dark green, leathery foliage; large, high-centered flowers, and a rich, coral orange flower color contrasted with a creamy reverse on the petal.

1 Drawing Sheet

The present invention relates to a new and distinct variety of rose plant of the hybrid tea class which was originated by the inventor by crossing an unnamed coral pink seedling with the variety JACpico, U.S. Plant Pat. No. 3,997.

The primary objective of this breeding was to produce a new rose variety having the exhibit flower form of the male parent JACpico combined with the coral pink flower color and higher petal count of the unnamed female parent. The objective was substantially achieved along with other desirable improvements as evidenced by the following unique combination of characteristics which are outstanding in the new variety and which distinguish it from its parents, as well as from all other varieties of which I am aware:

1. Large, high-centered blooms;
2. A rich coral orange color that deepens with age;
3. Vigorous, upright, well-branched plant;
4. Dark green, leathery, semi-glossy foliage; and
5. Long-lasting, long-stemmed cut roses.

Asexual reproduction of this new variety by budding, as performed as Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed coral pink seedling.

*Pollen parent.*—JACpico, U.S. Plant Pat. No. 3,997.

Classification:

*Botanical.*—*Rosa hybrida.*

*Commercial.*—Hybrid tea.

FLOWER

Observations made from specimens grown in a garden in Somis, Calif., from March through July, 1992.

Blooming habit: Recurrent.

Bud:

*Size.*—1½ inches when the petals start to unfurl.

*Form.*—Long, pointed ovoid.

*Color.*—When sepals first divide, bud color is Orange Red Group 35C. When half blown, the upper sides of the petals are Red Group 42B on the petal edge, becoming Red Group 42C in the middle, becoming near white for the inner third of the petal; and the lower sides of the petals are much lighter in color, near Red Group 36A except where exposed to the sun, where they are near Red Group 42C.

*Sepals.*—Color: Green Group 138C. Surface texture: Covered in fine hairs. There are three lightly appendaged sepals. There are two unappendaged sepals with hairy edges.

*Receptacle.*—Color: Green Group 139C. Shape: Apple. Size: Small (¼×¼ inch). Surface: Smooth.

*Peduncle.*—Length: Medium (3 inches). Surface: Smooth. Color: Light green. Strength: Stiff, erect.

Bloom:

*Size.*—Large. Average open size is 5 inches.

*Borne.*—Singly.

*Stems.*—Medium (16 to 18 inches); strong.

*Form.*—When first open: High centered. Permanence: Retains its form to the end, outer petals curl back.

*Petalage.*—Number of petals under normal conditions: 30 to 35.

*Color.*—The upper side of the petals is Red Group 42B on the petal edges, becoming Red Group 42C in the middle portion of the petal before becoming near white for the inner third of the petal. The reverse side of the petals is Red Group 36A except where exposed to the sun, where they are near Red Group 42C. The bases of petals have a small (⅛×⅛ inch) yellow half moon at the point of attachment. The major color on the upper side is Red Group 42B to C.

*Variegations.*—None.

*Discoloration.*—The general tonality at the end of the first day: Little change. At the end of the third day: Increase in the amount of the petal colored in Red Group 42B.

*Fragrance.*—Moderate.

Petals:
*Texture.*—Thick.
*Shape.*—Round.
*Form.*—Tips slightly recurved.
*Arrangement.*—Imbricated, with few petaloids in the center.
*Persistence.*—Drop off cleanly.
*Lastingness.*—On the plant: Long (5 to 7 days). As a cut flower: Long (7 to 8 days).

Reproductive parts:
*Anthers.*—Size: Medium. Quantity: Many. Color: Yellow. Arrangement: Regular around styles.
*Filaments.*—Color: Yellow.
*Pollen.*—Color: Lemon yellow.
*Styles.*—Color: Red.
*Stigmas.*—Color: Red.

Form: Bush.
Growth: Vigorous.

Foliage:
*Number of leaflets on normal mid-stem leaves.*—5 to 7.
*Size.*—Large (6×4 inches).
*Quantity.*—Abundant.
*Color.*—New foliage: Red. Old foliage: Dark green, semi-glossy.

Leaflets:
*Shape.*—Oval.
*Texture.*—Upper side: Leathery.
*Edge.*—Serrated.

*Serration.*—Single, small.
*Petiole rachis.*—Color: Green.
*Petiole underside.*—Smooth, with occasional prickles.
*Stipules.*—Medium, serrated.
*Disease resistance.*—Susceptible to mildew but resistant to rust under normal growing conditions at Somis, Calif.

Wood:
*New wood.*—Color: Reddish. Bark: Smooth.
*Old Wood.*—Color: Green. Bark: Smooth.

Prickles:
*Quantity.*—On main canes from base and on laterals from main canes: Ordinary.
*Form.*—Medium, hooked slightly downward.
*Color when young.*—Red.

Small prickles:
*Quantity.*—None on main stalks or on laterals.

I claim:

1. A new and distinct variety of rose plant of the hybrid tea class, substantally as herein shown and described, characterized particularly as to novelty by the unique combination of its production of long-lasting, long-stemmed cut roses; a vigorous, upright plant; dark green, leathery foliage; large, high-centered flowers, and a rich, coral orange flower color contrasted with a creamy reverse on the petal.

* * * * *

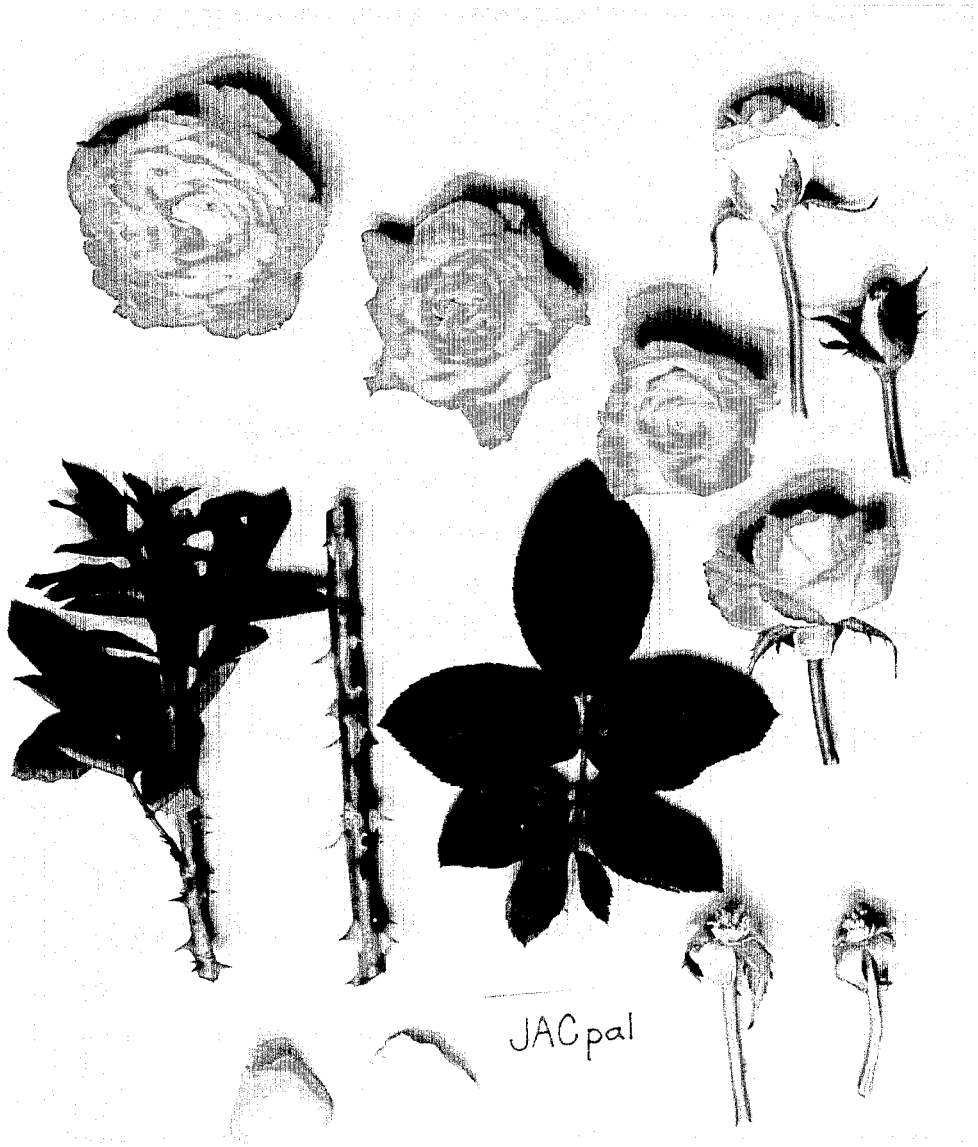
JACpal